(12) United States Patent
Adair

(10) Patent No.: US 7,110,808 B2
(45) Date of Patent: Sep. 19, 2006

(54) METHOD OF OPTIMIZING RADIOSURGERY AND RADIOTHERAPY WITH METALLOPORPHYRINS

(76) Inventor: Edwin L. Adair, 317 Paragon Way, Castle Pines Village, CO (US) 80104

( * ) Notice: Subject to any disclaimer, the term of this patent is extended or adjusted under 35 U.S.C. 154(b) by 0 days.

(21) Appl. No.: 10/836,454

(22) Filed: Apr. 30, 2004

(65) Prior Publication Data
US 2004/0202610 A1 Oct. 14, 2004

Related U.S. Application Data

(63) Continuation-in-part of application No. 10/176,558, filed on Jun. 21, 2002, now Pat. No. 6,750,037.

(51) Int. Cl.
*A61B 6/00* (2006.01)
(52) U.S. Cl. .............. 600/431; 600/436; 250/363.03; 378/65; 436/431; 540/145
(58) Field of Classification Search .............. 435/29, 435/4, 968, 283.1, 288.7; 702/40; 600/431, 600/436; 250/363.03; 378/65; 436/431; 514/185; 540/145
See application file for complete search history.

(56) References Cited

U.S. PATENT DOCUMENTS

| | | | |
|---|---|---|---|
| 3,846,490 A | 11/1974 | Aronova et al. | 562/567 |
| 3,934,369 A | 1/1976 | Rebeiz | 47/58 |
| 3,973,129 A | 8/1976 | Blumberg et al. | 250/461 B |
| 4,772,681 A | 9/1988 | Fukuda et al. | 540/145 |
| 4,886,831 A | 12/1989 | Morcos et al. | 514/456 |
| 4,897,444 A | 1/1990 | Brynes et al. | 525/54.1 |
| 4,905,670 A | 3/1990 | Adair | 128/18 |
| 4,920,143 A | 4/1990 | Levy et al. | 514/410 |
| 4,977,177 A | 12/1990 | Bommer et al. | 514/410 |
| 4,997,639 A | 3/1991 | Aizawa et al. | 424/9 |
| 5,026,368 A | 6/1991 | Adair | 606/15 |
| 5,043,101 A | 8/1991 | Gordon | 252/408.1 |
| 5,079,262 A | 1/1992 | Kennedy et al. | 514/561 |
| 5,087,636 A | 2/1992 | Jamieson et al. | 514/410 |
| 5,117,466 A | 5/1992 | Buican et al. | 382/6 |
| 5,122,453 A | 6/1992 | Martin et al. | 435/7.24 |
| 5,143,054 A | 9/1992 | Adair | 128/18 |
| 5,149,708 A | 9/1992 | Dolphin et al. | 514/410 |
| 5,162,231 A | 11/1992 | Cole et al. | 436/64 |
| 5,211,938 A | 5/1993 | Kennedy et al. | 424/7.1 |
| 5,234,940 A | 8/1993 | Kennedy et al. | 514/410 |
| 5,251,613 A | 10/1993 | Adair | 128/6 |
| 5,270,171 A | 12/1993 | Cercek et al. | 435/29 |
| 5,283,255 A | 2/1994 | Levy et al. | 514/410 |
| 5,308,608 A | 5/1994 | Dolphin et al. | 424/9 |
| 5,308,861 A | 5/1994 | Aizawa et al. | 514/410 |
| 5,391,547 A | 2/1995 | Cole et al. | 514/184 |
| 5,418,169 A | 5/1995 | Crissman et al. | 436/94 |
| 5,422,093 A | 6/1995 | Kennedy et al. | 424/9.61 |
| 5,441,531 A | 8/1995 | Zarate et al. | 607/90 |
| 5,554,505 A | 9/1996 | Hajek et al. | 435/721 |
| 5,556,764 A | 9/1996 | Sizto et al. | 435/7.24 |
| 5,591,422 A | 1/1997 | Hemmi et al. | 424/9.362 |
| 5,605,805 A | 2/1997 | Verwer et al. | 435/7.24 |
| 5,616,342 A | 4/1997 | Lyons | 424/450 |
| 5,627,040 A | 5/1997 | Bierre et al. | 435/7.24 |
| 5,652,114 A | 7/1997 | Chu et al. | 435/7.23 |
| 5,773,609 A | 6/1998 | Robinson et al. | 540/145 |
| 5,955,490 A | 9/1999 | Kennedy et al. | 514/410 |
| 5,986,693 A * | 11/1999 | Adair et al. | 348/76 |
| 6,190,877 B1 | 2/2001 | Adair | 435/29 |
| 6,235,767 B1 | 5/2001 | Kelly et al. | 514/410 |
| 6,358,989 B1 | 3/2002 | Kunz et al. | 514/411 |
| 6,387,350 B1 | 5/2002 | Goldenberg | 424/1.57 |
| 6,395,016 B1 | 5/2002 | Oron et al. | 607/88 |
| 6,422,988 B1 | 7/2002 | Bradshaw et al. | 600/3 |
| 6,422,989 B1 | 7/2002 | Hektner | 600/3 |
| 6,566,517 B1 | 5/2003 | Miura et al. | 540/145 |
| 6,750,037 B1 * | 6/2004 | Adair et al. | 435/29 |

FOREIGN PATENT DOCUMENTS

| EP | 0 277 837 | 10/1988 |
|---|---|---|
| JP | 04330013 A | 11/1992 |

OTHER PUBLICATIONS

U.S. Appl. No. 10/836,453, filed Apr. 2004, Adair.*
Palac et al; Nuclear Medicine Communications, V. 10(11), pp. 841-850, (Nov. 1989) (Abstract Only).*
Abstract, Mu Y, et al., "P-S-D-007 Luminescence in the Diagnosis of Exfoliative Cells from Malignant Tumors", X-P-0021614131, vol. 9, No. 4, 1987, pp. 258-259.
Abstract, Schwartz, G., et al., "Selected Amino Acridines as Fluorescent Probes in Cytochemistry in General and in the Detection of Cancer Cells in Particular", *Analytical and Quantitative Cytology*, vol. 4, No. 1, 1982, pp. 44-54.

(Continued)

*Primary Examiner*—Ralph Gitomer

(57) ABSTRACT

An apparatus and method for subsequent optimization of radiosurgery and radiotherapy is provided. The invention includes administering a metalloporphyrin to the patient, and then creating a 3-dimensional mapping of tissue through use of PET or SPECT. Malignant and pre-malignant tissue has an affinity for the metalloporphyrin. During treatment, real-time images are also provided which are compared to the previous 3-dimensional mapping. Creation of the real-time images is also achieved through PET or SPECT wherein a metalloporphyrin is administered to the patient. Total administration of radiation is calculated by summing radiation from the metalloporphyrins and from the radiosurgery/radiotherapy. The amount of radiation delivered by the metalloporphyrins and by the radiosurgery/radiotherapy are adjustable based on a patient's response to the dual delivery.

7 Claims, 1 Drawing Sheet

OTHER PUBLICATIONS

Abstract, Gardiner, R.A., et al., "Abnormal prostatic cells in ejaculates from men with prostatic cancer: A preliminary report", *British Journal of Urology*, vol. 78, No. 3, 1996, pp. 414-418.

Abstract, Bologna, M., et al., "Improved tissue culture method for the study of prostatic carcinoma: A significant diagnostic tool.", *Pathology Research and Practice*, vol. 191, No. 9, 1995, pp. 899-903.

Artemov et al., *Cancer Res.*, 61:3039-3044 (2001).

Fiel et al., *Cancer Letters*, 40:23-32 (1988).

Furmanski and Longley, *Cancer Res.*, 48:4604-4610 (1988).

Harisinghani et al., *N. Engl. J. Med.*, 348(25):2491-2499 (2003).

Koenig et al., *Magnetic Resonance in Medicine*, 4:252-260 (1987).

Lyon et al., *Magnetic Resonance in Medicine*, 4:24-33 (1987).

Rosenthal et al., *Clin. Cancer Res.*, 5:739-745 (1999).

van Zijl et al., *Acta Radiologica*, 374(supp):75-79 (1990).

Pottier et al.; "Non-Invasive Technique for Obtaining Fluorescence Excitation and Emission Spectra *In Vivo*"; *Photochemistry and Photobiology*; vol. 44, No. 5; pp. 679-687, 1986.

Abstract, Sauter, E.R., et al., "Nipple aspirate fluid: A promising non-invasive method to identify cellular markers of breast cancer risk", *British Journal of Cancer*, vol. 76, 1997, pp. 494-501.

Abstract, Sugiyama, M., et al., "Non-invasive detection of bladder cancer by identification of abnormal CD44 proteins in exfoliated cancer cells in urine", Abstract, *Clinical Molecular Pathology*, 1995, vol. 48, pp. M142-M147.

Nyamekye et al.; "Photodynamic Therapy of Normal and Balloon-Injured Rat Carotid Arteries Using 5-Amino-Levulinic Acid"; *Circulation*, vol. 91, No. 2, Jan. 15, 1995, pp. 417-425.

Peng et al.; "5-Aminolevulinic Acid-Based Photodynamic Therapy"; *American Cancer Society*; 1997; pp. 2282-2305.

Berg et al.; "The Influence of Iron Chelators On the Accumulation of Protoporphyrin IX in 5-Aminolaevulinic Acid-Treated Cells"; *British Journal of Cancer*; 1996; pp. 688-697.

Noodt et al.; "Apoptosis and Necrosis Induced With Light and 5-Aminolaevulinic Acid-Derived Protoporphyrin IX"; *Flow Cytometry*; 1996; pp. 22-29.

Malik et al.; "Destruction of Erythroleukaemic Cells by Photoactivation of Endogenous Porphyrins" *British Journal of Cancer*; 1987; 56; pp. 589-595.

Leon et al.; "Localized Intracoronary Gamma-Radiation Therapy to Inhibit the Rcurrence of Restenosis After Stenting"; *The New England Journal of Medicine*; Jan. 25, 2001; 344(4); pp. 250-256.

Verin et al.; "Endoluminal Beta-Radiation Therapy for the Prevention of Coronary Restenosis After Balloon Angioplasty"; *The New England Journal of Medicine*; Jan. 25, 2002; 344(4); pp. 243-249.

Abstract: Leunig et al.; "Fluorescence Photodetection of Neoplastic Lesions in the Oral Cavity Following Topical Application of 5-Aminolevulinic Acid"; *Laryngo-Rhino-Otologie*; vol. 75, No. 8, Aug. 1996; pp. 459-464.

Firnau et al.; "$^{64}$Cu Labelling of Hematoporphyrin Derivative for Non-Invasive In-Vivo Measurements of Tumour Uptake" *Porphyin Localization and Treatment of Tumors*; 1984 Alan R. Liss, Inc.; pp. 629-636.

Webster's II New Riverside University Dictionary, Copyright 1984, 1988, 1994, pp. 490 and 968.

News and Views; Radiolabelled photosensitizers for tumour imaging and photodynamic therapy, B.C. Wilson and J.E. VanLier; XPOO8023295, 459-463.

The Biological Characteristics of a Water Soluble Porphyrin in Rat Lymph Nodes; D.A. Cole, J.A. Mercer-Smith, S.A. Schreyer, J.K. Norman and D.K. Lavallee; XP008023296, 457-464.

Porphyrin Localization and Treatment of Tumors, pp. 629-636; 1984 Alan R. Liss, Inc., XP0080239292.

Chromatographic Analysis and tissue Distribution of Radiocopper-Labelled Haematoporphyrin Derivatives; Brian C. Wilson, Gunter Firnau, W. Patrick Jeeves, Kay L. Brown, Diane M. Burns-Mc-Cormick; XP008023291, 72-79.

* cited by examiner

METHOD OF OPTIMIZING RADIOSURGERY AND RADIOTHERAPY WITH METALLOPORPHYRINS

CROSS REFERENCE TO RELATED APPLICATIONS

This application is a continuation-in-part of application Ser. No. 10/176,558, filed on Jun. 21, 2002 now U.S. Pat. No. 6,750,037, entitled "Method of Cancer Screening Primarily Utilizing Non-Invasive Cell Collection, Fluorescence Detection Techniques, and Radio Tracing Detection Techniques", the disclosure of which is hereby incorporated by reference herein.

FIELD OF THE INVENTION

This invention relates to cancer screening and cancer treatment, and more particularly, to the use of metalloporphyrins for subsequent optimization of radiosurgery and/or radiotherapy.

BACKGROUND OF THE INVENTION

There are a number of prior art methods and apparatuses which are used in the detection and treatment of cancer. Fluorescent markers have been used to help identify cancerous tissue within a patient. Radio tracers or markers have also been used in the detection and treatment of cancer.

U.S. Pat. No. 5,391,547 discloses a method of using porphyrins to detect lung cancer, and more particularly, to the use of tetra-aryl porphyrins. The porphyrins are used as a fluorescent tracer for cancers of the lung. The porphyrins may be complexed with Copper 64 ($^{64}$Cu) or Copper 67 ($^{67}$Cu). Thus, the complex can be used as radio tracers as well. The $^{67}$Cu provides a source of beta radiation for selective destruction of lung malignancies as well as gamma radiation useful for image analysis, as by single photon emission computer tomography. The $^{64}$Cu may be used for radio tracing wherein a positron emission tomography technique can be used to locate the malignant tissue.

U.S. Pat. No. 5,087,636 to Jamieson, et al. discloses a method to identify and destroy malignant cells in mononuclear cell populations. This method includes the steps of contacting a composition of bone marrow cells or other cells with a green porphyrin of a specific compound, irradiating the cell composition with light at a wave length effective to excite fluorescence of the green porphyrin, and then detecting the presence or absence of fluorescence indicating malignancy. This reference also discloses the steps by which the bone marrow cells are removed, separated, washed and diluted to an appropriate concentration for treatment, incubated, centrifuged, and exposed to the irradiating light.

U.S. Pat. Nos. 5,308,608 and 5,149,708 to Dolphin, et al. disclose specific types of porphyrin compounds which may be used for detection, photosensitization, or the destruction of a targeted biological material when the targeted tissue is contacted with the specified porphyrin, and irradiated with light that excites the compound.

U.S. Pat. No. 5,211,938 to Kennedy, et al. discloses a method of detection of malignant and non-malignant lesions by photo chemotherapy of protoporphyrin IX precursors. 5-amino levulinic acid (5-ALA) is administered to the patient in an amount sufficient to induce synthesis of protoporphyrin IX in the lesions, followed by exposure of the treated lesion to a photo activating light in the range of 350–640 nanometers. Naturally-occurring protoporphyrin IX is activatable by light which is in the incident red light range (600–700 nanometers) which more easily passes through human tissue as compared to light of other wave lengths which must be used with other types of porphyrins. In short, the use of 5-ALA makes cell fluorescence easier to observe, and also greatly reduces the danger of accidental phototoxic skin reactions in the days following treatment since protoporphyrin IX precursors have a much shorter half life in normal tissues than other popularly used porphyrins.

Present methods relating to cancer screening using fluorescence detection systems require the use of interventional devices such as endoscopes which have the special capability of delivering specified light frequencies to a targeted tissue of a patient. These endoscopes illuminate the targeted part of the body in which cancer is suspected. The light delivered at a specified frequency illuminates an area which has previously been subjected to some type of fluorescent marker, such as a porphyrin which causes malignant cells to illuminate or fluoresce under observation of light at the specified frequency. In all cases, introduction of an endoscope into the body requires some type of sedation or general or local anesthesia. Once a tumor has been located by use of the interventional device, depending upon the type of tumor, photo chemotherapy or other treatment means can be used. However, prior to actual treatment, there must be a confirmed test of cancer. Accordingly, the tumor still needs to be sampled by an appropriate biopsy method. Generally, biopsy methods also require some type of sedation or anesthesia. Thus, traditional methods of confirming a malignancy may require at least two interventional surgical procedures.

In all uses of photodynamic therapy, it is well known that there are limitations in such therapy because of the poor penetration of the visible light required to activate the administered porophyrin so as to render it toxic to the targeted tissue. Particularly for tumors which are found deep within the body of a patient, repeated interventional procedures to treat the neoplastic tissue become infeasible. Accordingly, many types of diseased tissue cannot be effectively treated through photodynamic therapy.

Stereotaxic radio surgery is a well known procedure to treat tumorous tissue. This type of radio surgery is particularly well known for treating brain tumors. Advances in technology for delivering a collimated surgical ionizing beam now allows medical personnel to treat patients with cancerous tissue throughout the body.

One company that provides a stereotaxic radio surgery system is Accuray of Boulder, Colo. One system developed by Accuray includes the Cyberknife™ system that incorporates a linear accelerator mounted on a robotic arm thereby providing a surgeon with great flexibility in delivering a collimated beam to a targeted area. The Cyberknife has been used to radiosurgically treat many tumors and other malformations at body sites which are unreachable by other stereotaxic systems.

Accuray is the owner of two U.S. patents which claim devices and methods of carrying out stereotaxic radio surgery and radio therapy. U.S. Pat. No. 5,207,223 discloses a method and apparatus for selectively irradiating a target within a patient. A 3-dimensional mapping is provided of a region surrounding the target. A beaming apparatus emits a collimated beam. Diagnostic beams at a known non-zero angle to one another pass through the mapping region. Images of projections are produced within the mapping region. Electronic representations of the images are compared with reference data from the 3-dimensional mapping thereby locating the target. The relative positions of the beaming apparatus and the living organism are adjusted in such a manner that the collimated beam is focused on the target region despite any movement by the patient during treatment. A comparison is repeated at small time intervals and, when the comparison so indicates, adjustment is repeated, as needed, and in such a manner that the collimated beam remains focused on the target region.

U.S. Pat. No. 5,427,097 owned by Accuray discloses another apparatus and method of performing stereotaxic surgery. A robotic arm and beam generating arrangement are provided along a predetermined, non-circular and non-linear path transverse to a collimated beam path, while at the same time, the collimated beam path is directed into the target region. Thus, the radiosurgical/radiotheraputic beam can be directed through the target region from particular treatment points along the transverse path so as to define a non-spherical target region, thereby allowing treatment of irregularly shaped tumors or malformations.

One important objective of the inventions disclosed in these references owned by Accuray is to improve the ability to deliver a radiological beam which can be precisely targeted for irradiating targeted tissue, yet limiting exposure of healthy tissue. With the inventions disclosed in the two references, it is possible to perform multiple fraction radiological treatment thereby improving the ability to target and localize cancerous or malformed tissue.

While the two references discussed immediately above represent advances in stereotaxic radiosurgery and radiotherapy, these systems can be further enhanced by improving the ability to not only map targeted tissue, but also to image the tissue during the radio surgery/radio therapy procedure thereby ensuring that the radiological beam is precisely aligned with the targeted tissue. In the above references, 3-dimensional mapping is obtained by a CAT scan (CT) or by magnetic resonance imaging (MRI). As is well known, computerized tomography operates through measurement of the differential absorption of x-ray beams, and the resulting images are in the form of data which is mathematically manipulated through Fourier transform. MRI utilizes nuclear magnetic resonance properties of tissue to obtain 3-dimensional mapping. CT scanners and MRI scanners are available commercially, and the data obtained by the scanning can be placed in a digitized format whereby it can be stored and manipulated through software in a computer. Although an MRI or CT scan may be adequate under many circumstances, the disadvantages of CT scanning or MRI scanning is that these types of scans image the physical structure of tissue, and do not provide information regarding the body's chemistry, or cell function.

More recent imaging technologies include positron emission tomography (PET). A PET scan differs from the CT or MRI scan in that the PET scan analyzes cell function, which in many instances provides a better method by which to determine whether tissue is cancerous. PET typically involves the administration of a radioactive form of glucose, and then the PET scanner tracks and records signals which are emitted by the administered compound. Actively growing cancer cells typically have much higher metabolic rates than normal cells; therefore, the radioactive glucose is metabolized more quickly by these cancerous tissues, thereby creating distinct signals which can be recorded by the PET scanner. A computer then reconstructs the recorded signals into 3-dimensional digital images that show areas throughout the body where diseases are present. In addition to PET, a related imaging technology includes single photon emission computer tomography (SPECT) which is also a computerized imaging technique that produces 3-dimensional images of tissue function. As with PET scanning, a small amount of a radioactive isotope is administered to a patient, and any increased metabolic activity present at various body locations can be identified and reviewed to determine whether a patient has diseased or cancerous tissue.

One class of chemicals useful for the treatment of tumors is the porphyrins and particularly hematoporphyrin derivatives. These chemicals have been studied as a result of their selective localization and uptake into tumors and malignant tissue and their sensitization of tumor tissues to photoirradiation. It has also been suggested that these chemicals could function as delivery vehicles to target other anticancer compounds to tumor tissues due to their selective uptake into tumor tissues. For example, porphyrin molecules may chelate one of many different metal atoms which are then localized to tumor tissues. These metal atoms can be radioactive isotopes which then irradiate the surrounding tumor tissue after localization to the tumor within a metalloporphyrin. Additionally, the radioactivity emitted can be used in PET or SPECT scanning to create an image of the tumor tissue. However, even without a radioactive component, the metalloporphyrins are still effective in selectively delivering a metal atom to tumor tissues. The metal can then act as a contrast agent to enhance magnetic resonance imaging or nuclear magnetic resonance imaging. Because the localization of the metalloporphyrins is based on the chemical properties of the porphyrins themselves and their interaction with characteristics of tumor cells including large interstitial space, high capillary permeability and lack of lymphatic drainage, and not on differences in metabolic activities in tissues, they are more selectively taken up and retained by malignant cells than are radioactive glucose molecules. For this reason, the metalloporphyrins are also better contrast agents for use with the different tumor imaging techniques than are radioactive glucose molecules.

One reference that discloses the use of metalloporphyrins as imageable tumor targeting agents for radiation therapy is U.S. Pat. No. 6,566,517. This reference specifically discloses halogenated derivatives of boronated porphyrins containing multiple carborane cages which selectively accumulate in neoplastic tissue, and thus can be used in cancer therapies including boron neutron capture therapy and photodynamic therapy. Although this reference generally discusses the uses of metalloporphyrins for radiation therapy, there is no disclosure of particular procedures by which targeted tissue can be mapped, nor is there disclosure of other methods by which cancer screening or treatment therapy can be conducted other than by boron neutron capture or photodynamic therapy.

SUMMARY OF THE INVENTION

The present invention provides a method and apparatus including use of metalloporphyrins for subsequent optimization of radio surgery and radio therapy.

The present invention may make use of porphyrin compounds complexed with various metals such as silver (Ag), aluminum (Al), cadmium (Cd), cobalt (Co), chromium (Cr), copper (Cu), iron (Fe), gadolinium (Gd), indium (In), lutetium (Lu), magnesium (Mg), manganese (Mn), nickel (Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn). These complexes are generally categorized as metalloporphyrins meaning a porphyrin moiety having a chelated radioactive isotope of a metal atom. These metalloporphyrins are further processed so that the metal is in the form of a radioactive isotope. The resulting radioactive metalloporphyrins thereby constitute radiopharmaceuticals that can be intravenously introduced to the patient. The affinity of neoplastic tissue for porphyrins results in selective uptake of the radioactive metalloporphyrin, thereby effecting targeted delivery of therapeutic radiopharmaceuticals. For example, in the instance of elemental copper chelated by the porphyrin, the copper can be transformed to radioactive $^{67}$Cu. In this way, introduction of the metalloporphyrin radiopharmacuetical to the patient is an effective means to deliver measured radiation therapy to targeted tissue. More specifically, $^{67}$Cu provides a source of beta radiation for selective destruction of neoplastic sites. Additionally, metalloporphyrin complexes still provide the ability to simultaneously conduct fluorescence detection and phototherapy if desired. Also, the metalloporphyrins provide the ability for observation of the targeted areas through PET (for example, through the use of $^{64}$Cu) or SPECT (for example, through use the of $^{67}$Cu).

A selected group of porphyrin compounds complexed with various metals are specifically contemplated in the present invention because these metalloporphyrins are particularly effective in tumor tissue imaging. The synthetic water soluble porphyrins which contain hydrophilic groups peripheral to the porphyrin ring facilitate oral administration and avoid the use of additional solubilizing agents. Fe(III) and Mn(III)meso-tetra(4-sulfonatophenyl)porphine (TPPS$_4$) are water soluble metalloporphyrins that show an increased affinity for solid tumor cells. This affinity is higher than would be expected for the metalloporphyrins as a general class of compounds. Without intending to be bound by any one theory, it is believed that this increased affinity for solid tumors results from the large size of these metalloporphyrins favoring their retention in the high capacity interstitial space of tumors. Additional factors believed to influence the selective accumulation of the metalloporphyrins in tumors includes charge on the peripheral substituents on the porphyrin ring at physiological pH as well as the plasma binding characteristics of the specific metalloporphyrin. Additionally, Fe(III) and Mn(III)TPPS$_4$ are very stable compounds making them easier to produce, ship and handle either in their non-radioactive form or having radioactive isotopes of iron or manganese atoms. Iron is known to have seven radioisotopes ($^{52}$Fe, $^{53}$Fe, $^{55}$Fe, $^{59}$Fe, $^{60}$Fe, $^{61}$Fe, $^{62}$Fe) and manganese is known to have six radioisotopes ($^{51}$Mn, $^{52}$Mn, $^{53}$Mn, $^{54}$Mn, $^{55}$Mn, $^{56}$Mn, $^{57}$Mn) providing many radioisotopes that can be used in the TPPS$_4$ prophyrin molecule. Each of these isotopes can be selected for the desired characteristics in terms of half life and emission spectra that make for the best use in producing, shipping and using the radioisotope in the scanning procedure. For example, $^{59}$Fe has a half life about 44.5 days while $^{62}$Fe has a half life of about 68 seconds. Similarly, $^{54}$Mn has a half life of 312 days whereas $^{57}$Mn has a half life of about 1.5 minutes. Thus, the desired radioisotope of these two metal atoms can be selected depending on the photon emission characteristics and a suitable or desired half-life. Table I contains a list of the radioisotopes of these two metal atoms and their half-lives. Therefore, the Fe(III) and Mn(III) derivatives of TPPS$_4$ having a radiometal capable of photo emission are preferred metalloporphyrins for use in the radiosurgery imaging techniques of the present invention.

TABLE I

| Radioisotope | Half-life |
| --- | --- |
| $^{52}$Fe | 8.28 hours |
| $^{53}$Fe | 8.51 minutes |
| $^{55}$Fe | 2.73 years |
| $^{59}$Fe | 44.51 days |
| $^{60}$Fe | 1.5 million years |
| $^{61}$Fe | 6 minutes |
| $^{62}$Fe | 68 seconds |
| $^{51}$Mn | 46.2 minutes |
| $^{52}$Mn | 5.59 days |
| $^{53}$Mn | 3.7 million years |
| $^{54}$Mn | 312.2 days |
| $^{56}$Mn | 2.58 hours |
| $^{57}$Mn | 1.45 minutes |

In accordance with the present invention, the desired metalloporphyrin may be administered directly to the patient orally, topically, or intravenously. Depending upon the compound introduced, a particular waiting period is necessary for uptake of the porphyrin compound. After sufficient time has been provided for a reaction between the compound and the targeted cells, a cancer screening procedure may take place wherein the patient is subject to an initial PET or SPECT procedure, and either a particular location may be imaged, or the entire body may be imaged, for example, to determine the extent to which a tumor has metastasized. After conducting the initial imaging procedure, 3-dimensional images of targeted body locations are created through mapping and the images are stored in a computer.

Based upon the results of the initial scanning procedure, subsequent radiosurgery/radiotherapy may take place. In the preferred embodiment, the particular stereotaxic radiosurgery procedure that is contemplated is the same as that disclosed in the above-mentioned U.S. Pat. Nos. 5,207,223 and 5,427,097, these references being incorporated herein by reference in their entireties. The present invention differs from the procedures disclosed in these prior art references by the method in which tissue is imaged. Instead of a CAT scan or MRI scan, 3-dimensional mapping is achieved by PET or SPECT scanning.

After mapping has been achieved, a beaming apparatus is provided to generate a collimated surgical ionizing beam of a sufficient strength to cause a targeted region to become necrotic. A preferred beaming apparatus includes an x-ray linear accelerator, although other ionizing radiation sources can be used. Means are provided which allow the collimated beam to be precisely aligned with the targeted area through a comparison of imaging data which takes place in real-time during treatment and the previously mapped images. The imaging which takes place during the treatment according to the present invention also includes imaging achieved by PET or SPECT. Assuming the time between creating the mapping images and treatment by use of the ionizing beam extends beyond the effective half-life of the metalloporphyrin, a metalloporphyrin is again administered to the patient prior to the treatment, and the metalloporphyrin metabolized in neoplastic tissue allows a very distinct target by which the collimated beam can be aligned. Images which are obtained real-time during treatment are compared with the previous mapped images, and the collimated beam is adjusted as necessary to maintain the collimated beam in alignment with its targeted location.

By the use of a metalloporphyrin administered to the patient, additional options are provided in treating cancerous or suspect tissue through radiation therapy/radiosurgical procedures. The metalloporphyrin can be specifically formulated to provide a desired amount of radiation which will not only allow 3-dimensional mapping during a PET/SPECT scanning, but may also provide radiation for treatment by exposure of the suspect tissue during the time in which the metalloporphyrin is metabolized by the tissue. The later radiosurgical procedure by use of an irradiating beam can be dosed to provide the amount of radiation necessary to provide the additional treatment necessary. Accordingly, the initial exposure of the tissue to the metalloporphyrin may result in desired treatment to a specific level, and the remaining required treatment can then be provided by the irradiating beam. Accordingly, the present invention has great flexibility in delivering radiation in two separate ways, namely, the administration of the metalloporphyrin and the use of an irradiating beam. If two administrations of a metalloporphyrin are required (i.e., once for mapping and once for providing real-time images), then the administrations are collectively dosed to deliver the desired amount of radiation.

One clear advantage to the above method is that in many instances, administration of the metalloporphyrin will greatly shrink a tumor size; therefore, the beam of radiation can be better focused onto a specific targeted area thereby further eliminating exposure of healthy tissue to the irradiating beam.

Thus, with the present invention, radiosurgery/radiotherapy can be optimized in a manner which enhances the ability to provide a radiosurgical beam to targeted areas in the body and to limit the adverse effects of radiation exposure of healthy tissue.

DETAILED DESCRIPTION

Figure 1:
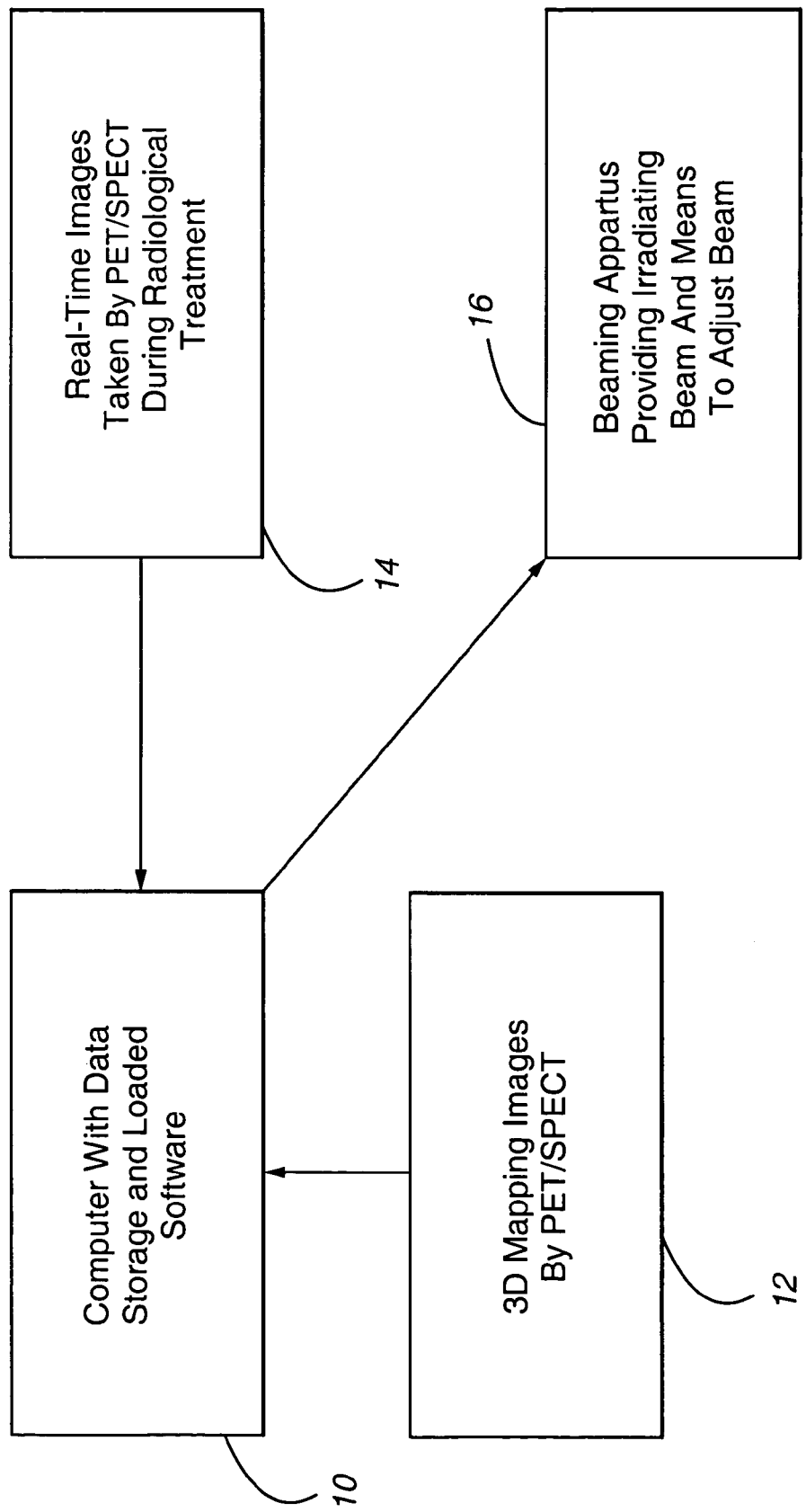
FIG. 1 is a block diagram illustrating the major components enabling completion of the method of the present invention.

In order to execute the method and apparatus of the present invention, a system is provided for delivering a collimated ionizing beam of radiation to a targeted area of tissue. Examples of such systems to support the present invention are disclosed in the U.S. Pat. Nos. 5,427,097 and 5,207,223.

Referring to FIG. 1, a representative system to achieve the present invention includes a computer 10 with data storage capability that is capable of executing instructions from software loaded within the computer. The computer can store and manipulate 3-dimensional mapping data images 12 of a patient being treated. The 3-dimensional mapping is typically stored in digital form, and is loaded in the computer 10 for later comparison purposes. As mentioned above, the 3-dimensional mapping is preferably achieved by SPECT or PET scanning following administration of a metaloporphyrin to a patient. A beaming apparatus 16 is provided which, when activated, emits a collimated surgical ionizing beam of a sufficient strength to cause a targeted region to become necrotic. Means are provided for generating real-time images 14 of tissue at and around the area which is being treated by the collimated beam during the stereotaxic radiosurgery/radiotherapy. In one form, the real-time images may be created by passing first and second diagnostic beams through the mapping region, the beams being laterally extensive to provide projections of the mapping region such as disclosed in the U.S. Pat. No. 5,207,223. However, the preferred manner in which to provide real-time images for comparison of the previous 3-dimensional mapping is to conduct an additional PET or SPECT procedure. These images 14 in digital form are then loaded into the computer 10, and software in the computer then compares the previous 3-dimensional mapping to the real-time images to determine the extent to which the collimated beam must be shifted or adjusted to irradiate the desired tissue. In response to comparison of the real-time images to the previous 3-dimensional mapping, means are provided for adjusting the relative position of the beaming apparatus 16 thereby adjusting the collimated beam to irradiate the desired target. As disclosed in the U.S. Pat. No. 5,427,09, one means to provide adjustment is through a robotic arm which precisely adjusts the collimated beam.

Because images which are taken by the PET or SPECT procedures are of such high quality and very accurately image tissue in three dimensions, the collimated beam can be better controlled, and the strength and duration of the beam can be minimized to provide only the amount of radiation necessary to treat targeted tissue, thereby minimizing exposure of healthy tissue to the radiation.

If it is desired to perform multiple fraction stereotaxic radiation, such treatment can be provided without having to use fiducials or other markers since the metalloporphyrins will efficiently localize in cancerous tissue, and the images are of such high quality that apparatuses such as a fiducials are therefore unnecessary to provide reference points to help locate suspect areas.

Radiation therapy can be delivered to a patient in the present method in multiple ways. The initial administration of the metalloporphyrin may have significant therapeutic results, and stereotaxic radiation can then complete the necessary radiation treatment. The dosages of radiation provided both by the metalloporphyrin and the irradiating beam can be selectively adjusted to provide the desired level of treatment. In any case, use of the irradiating beam to treat suspect tissue can be better delivered to the patient because PET/SPECT precisely images suspect tissue. Thus, the irradiating beam can thereby be better aligned and minimized in strength and duration to irradiate only the target region thereby minimizing exposure of healthy tissue that surrounds the suspect tissue.

While the present invention has been described in connection with a specific preferred embodiment, it shall be understood that various modifications to the present invention can be made within the spirit and the scope of the present invention as defined by the appended claims.

What is claimed is:

1. A method of selectively irradiating a target region of tissue comprising:

administering a metalloporphyrin to a patient;

conducting PET or SPECT to prepare a 3-dimensional image representative of a mapping region of at least a portion of the patient to be treated, the mapping covering an area of the patient larger than a target region, the administered metalloporphyrin enabling high quality imaging through PET or SPECT;

storing the mapping as reference data in digital form;

positioning the patient with the mapping region within the target region of a radiosurgical beaming apparatus;

activating the beaming apparatus to emit a radiosurgical beam to cause the target region to become necrotic;

conducting another PET or SPECT during the time in which the radiosurgical beaming apparatus is activated;

producing electronic images representative of the PET or SPECT taken during activation of the beaming apparatus;

comparing the images taken during mapping with the images taken during activation of the beam to provide position data representative of relative spatial locations of the beam and of the target region;

adjusting the relative position of the beaming apparatus in such a manner that the beam is focused onto the target region maintaining the beaming apparatus in its activated state for the time necessary to provide a desired amount of radiation;

completing said comparing step at selected time intervals using newly produced real-time images such that any movement of the target region relative to a focus of the beam is detected in substantially real-time; and repeating said adjusting step, as needed, to maintain focus of the beam on the target region.

2. A method, as claimed in claim 1, that further comprises, prior to the step of activating the beaming apparatus:

selecting the metalloporphyrin which provides a measured and desired amount of radiation therapy to a target region; and adjusting the amount of radiation provided by the radiosurgical beam to account for radiation therapy which has already occurred due to radiation therapy provided by the metalloporphyrin.

3. A method, as claimed in claim 1, wherein:
the radiosurgical beam is an x-ray beam.

4. A method, as claimed in claim 1, wherein:
the selected total dose of radiation is determined by measuring the amount of radiation provided by administration of the metalloporphyrin, and summing such amount with the amount of radiation that is provided by the radiosurgical beam.

5. A method, as claimed in claim 1, wherein:
said administering step occurs with first administration of the metalloporphyrin prior to said first conducting step, and said administering step occurs in a second administration of the metalloporphyrin after said storing step, and wherein the amount of radiation provided in twice administering the metalloporphyrin is summed with the amount of radiation provided by the radiosurgical beam to determine a total amount of radiation delivered to the patient.

6. A method as claimed in claim 1, wherein:
said metalloporphyrin is meso-tetra(4-sulfonatophenyl) porphine complexed with a radiometal imageable by SPECT or PET imaging selected from the group consisting of manganese and iron.

7. A method of optimizing radiosurgery/radiotherapy by selectively irradiating a targeted area of tissue, said method comprising the steps of:

administering a radio-imageable form of the metalloporphyrin Mn(III)meso-tetra (4-sulfonatophenyl)porphine to a patient;

conducting PET or SPECT to prepare a 3-dimensional image representative of a mapping region of at least a portion of the patient to be treated, the mapping covering an area of the patient larger than a target region, the administered metalloporphyrin enabling high quality imaging through PET or SPECT;

storing the mapping as reference data in digital form;

positioning the patient with the mapping region within the target region of a radiosurgical X-ray beaming apparatus;

selecting a total dose of radiation by measuring the amount of radiation provided by administration of the metalloporphyrin, and summing such amount with the amount of radiation that is provided by the X-ray radiosurgical beam;

adjusting the amount of radiation provided by the radiosurgical X-ray beam to account for radiation therapy which has already occurred due to radiation therapy provided by the metalloporphyrin;

activating the X-ray beaming apparatus to emit an X-ray beam to cause the target region to become necrotic;

conducting another PET or SPECT during the time in which the radiosurgical X-ray beaming apparatus is activated;

producing electronic images representative of the PET or SPECT taken during activation of the x-ray beaming apparatus;

comparing the images taken during mapping with the images taken during activation of the X-ray beam to provide position data representative of relative spacial locations of the beam and of the target region;

adjusting the relative position of the X-ray beaming apparatus in such a manner that the beam is focused onto the target region maintaining the beaming apparatus in its activated state for the time necessary to provide a desired amount of radiation;

completing said comparing step at selected time intervals using newly produced real-time images such that any movement of the target region relative to a focus of the X-ray beam is detected in substantially real-time; and repeating said adjusting step, as needed, to maintain focus of the X-ray beam on the target region.

* * * * *